United States Patent [19]
Wicherski et al.

[11] Patent Number: 5,107,990
[45] Date of Patent: Apr. 28, 1992

[54] RIGID CLOSURE LID TO A DISPOSABLE CONTAINER FOR HOLDING AND DISPOSING OF USED MEDICAL SHARPS AND OTHER MEDICAL-SURGICAL MATERIALS

[75] Inventors: Jan A. Wicherski, Palm Springs; Willaim L. Noack, Camarillo, both of Calif.

[73] Assignee: Devon Industries, Inc., Chatsworth, Calif.

[21] Appl. No.: 495,453

[22] Filed: Mar. 14, 1990

[51] Int. Cl.⁵ ............................................. B65D 83/10
[52] U.S. Cl. .................................. 206/366; 206/370; 206/1.5; 220/345; 220/346; 220/908
[58] Field of Search ............... 206/1.5, 45.34, 365, 206/366, 370, 807, 439; 220/1 T, 345, 346, 347, 908; 232/43.1, 43.2, 43.5, 44

[56] References Cited

U.S. PATENT DOCUMENTS

| | | | |
|---|---|---|---|
| 3,362,564 | 1/1968 | Mueller | 220/346 |
| 3,494,458 | 2/1970 | Meierhoefer | 206/366 |
| 3,527,373 | 9/1970 | Giraudet et al. | 220/345 |
| 3,531,012 | 9/1970 | Bergh et al. | 220/345 |
| 3,791,514 | 2/1974 | Watanabe . | |
| 4,120,400 | 10/1978 | Kotyuk | 220/346 |
| 4,548,688 | 4/1986 | Harris et al. | 220/1 T |
| 4,634,004 | 1/1987 | Mortensen | 206/1.5 |
| 4,728,504 | 3/1988 | Nichols | 206/439 |
| 4,736,860 | 4/1988 | Bemis | 220/1 T |
| 4,782,942 | 11/1988 | Ashley et al. | 206/439 |
| 4,804,090 | 2/1989 | Schuh et al. | 220/1 T |
| 4,828,107 | 5/1989 | Spencer | 206/366 |
| 4,842,138 | 6/1989 | Sandel et al. | 206/370 |
| 4,863,023 | 9/1989 | Payne et al. | 206/45.34 |
| 4,874,103 | 10/1989 | Quisenberry et al. | 206/366 |
| 4,900,519 | 2/1990 | Nichols | 206/439 |
| 4,921,097 | 5/1990 | Finke et al. | 206/45.34 |

Primary Examiner—David T. Fidei
Attorney, Agent, or Firm—Poms, Smith, Lande & Rose

[57] ABSTRACT

A closure lid for a rigid, disposable container for safely containing and disposing of medical-surgical materials, including needles, syringes, scalpels and dressings after use, comprises two lightweight plastic pieces which snap together without tools to form a closed container having a large opening for the insertion of used materials therethrough, which opening can be permanently sealed by sliding a flush cover to a closed and locked position preventing the inadvertent expulsion of macroscopic material from within the container. A one-way barrier is provided at the large opening for the protection of the user, which barrier can be removed if desired, and additional apertures having sharps-removing features molded therein to permit the simultaneous removal of sharps from associated devices and their disposal therethrough.

8 Claims, 3 Drawing Sheets

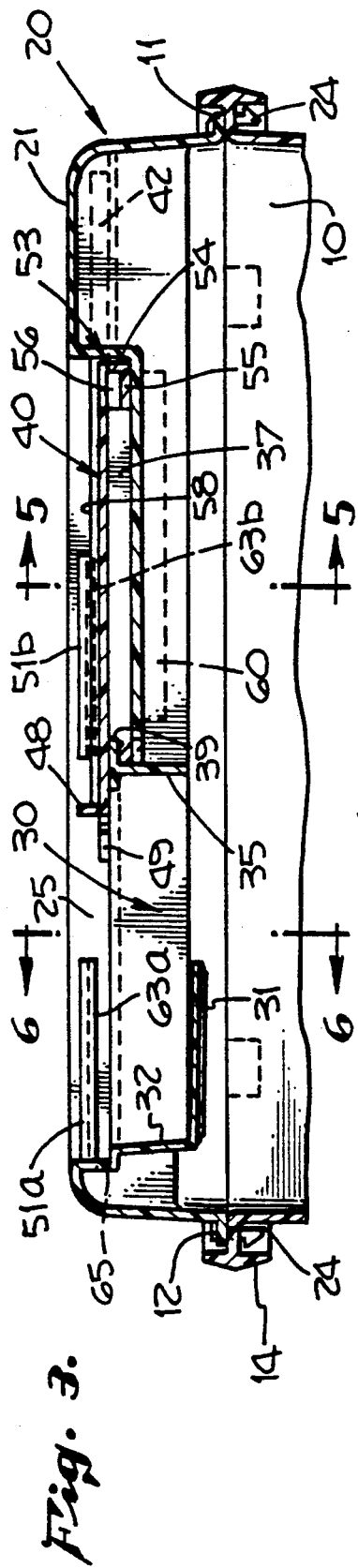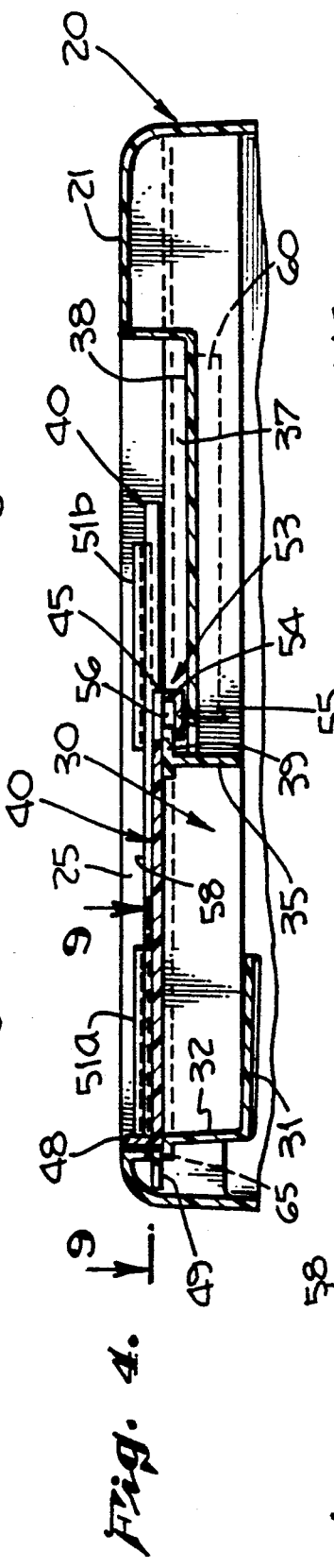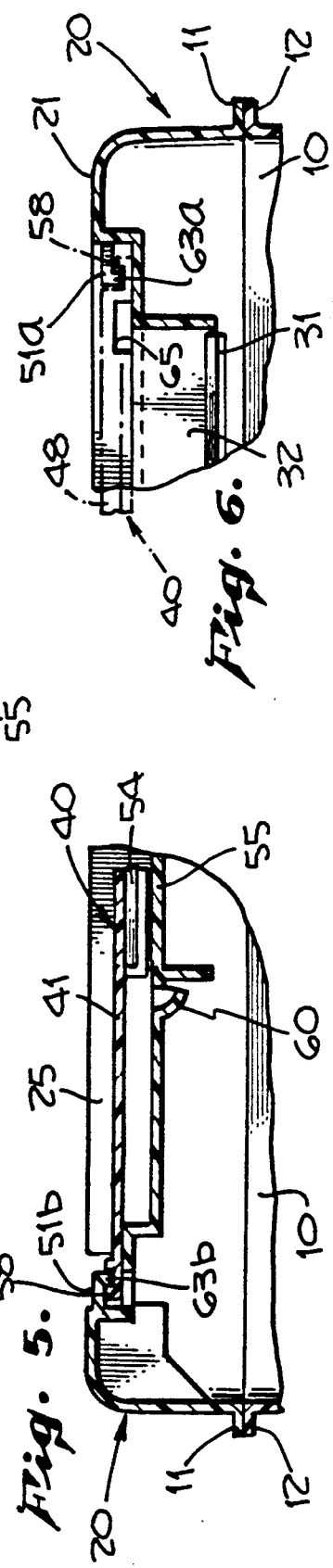

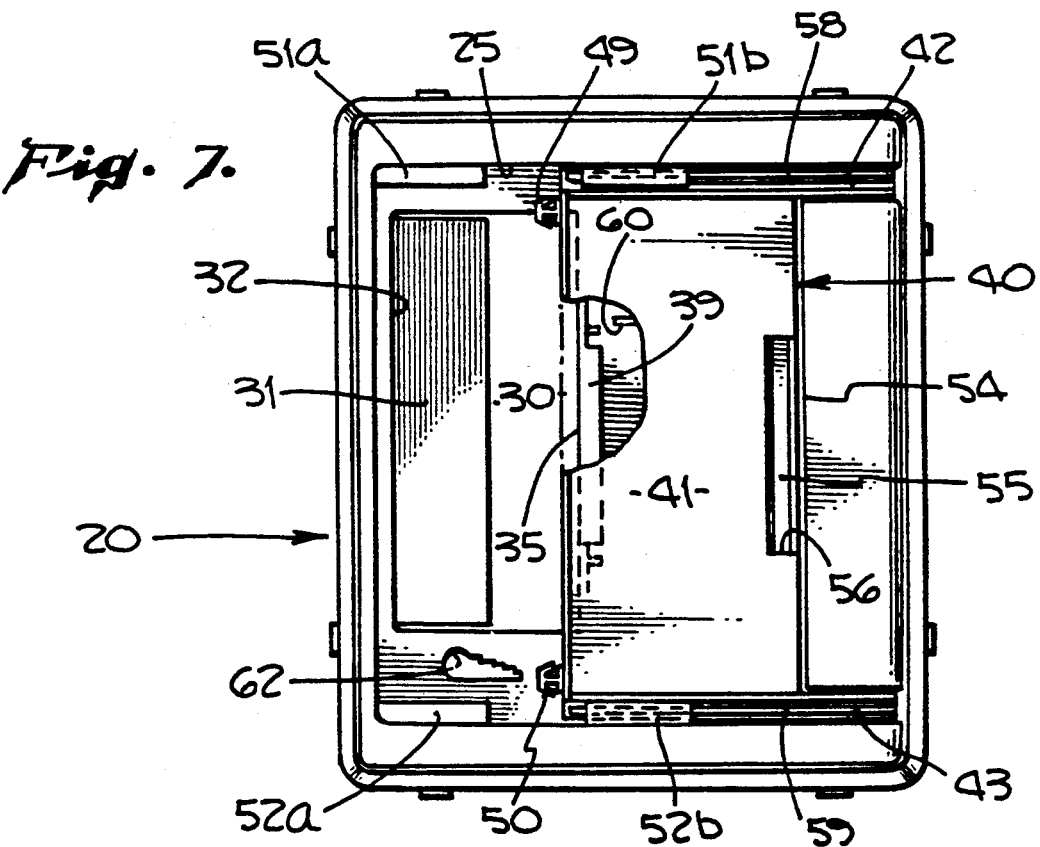
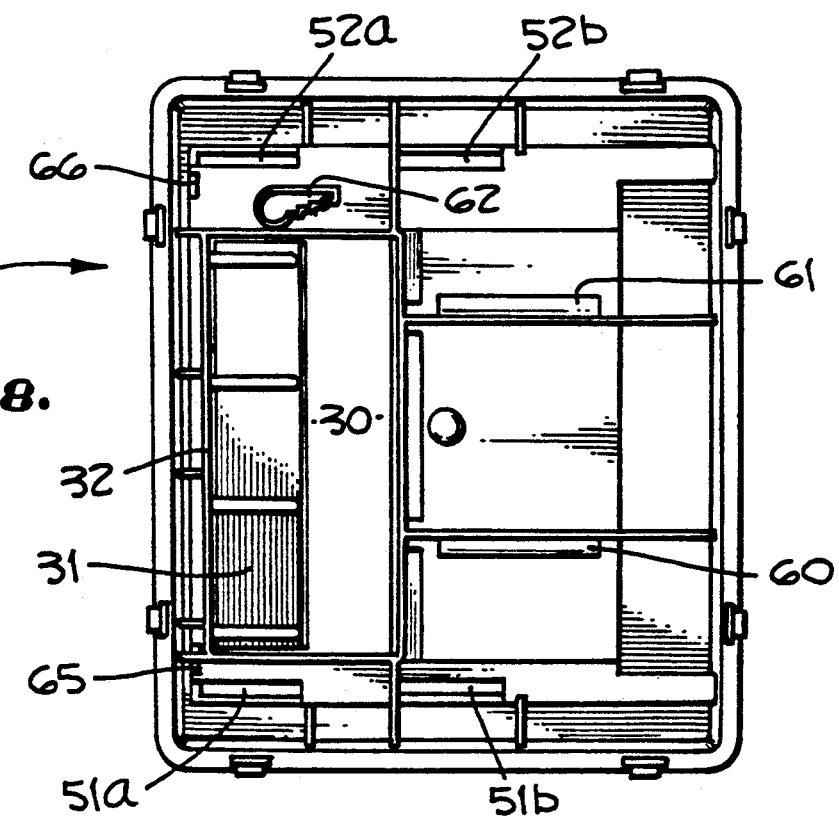

RIGID CLOSURE LID TO A DISPOSABLE CONTAINER FOR HOLDING AND DISPOSING OF USED MEDICAL SHARPS AND OTHER MEDICAL-SURGICAL MATERIALS

BACKGROUND OF THE INVENTION

1. Field of the Invention

This invention relates, in general, to medical-surgical supplies for hospitals, and more particularly to rigid, disposable containers for used medical-surgical materials, including "sharps," e.g., hypodermic needles, suture needles and scalpel blades.

2. Summary of the Prior Art

This decade has seen an acceleration of the trend in the medical care provision field of disposable, one-use medical-surgical devices and materials. This trend is away from the former procedure of sterilization and reuse of these devices, both to reduce the high labor costs involved in the sterilization and to ensure that materials and devices used are completely sterile. Cost tradeoffs have shown this use-and-dispose philosophy compares quite favorably with the previous method.

Present hospital protocol in those institutions employing the use-and-dispose philosophy entails the assembly and distribution by unskilled personnel of a clean, but not sterilized, flexible plastic or paper container to those locations where containment is required, viz., operating rooms, nurses' stations, soiled linen rooms and emergency rooms.

These containers may be used in the "sterile field" of the operating room, for example, on the "back table" when it is in the sterile field of the operating room or outside of the sterile field, where the "sterile nurse" passes the used materials to be disposed of to the "circulating nurse," who then disposes of the materials in the container.

After the containers are filled, they are typically collected by unskilled housekeeping personnel and taken for disposal. In some states this involves processing of the used materials by incineration, and in some states, by law, the materials are "red-bagged" or boxed, and stored for pickup by contract disposal personnel. They, in turn, transport the materials to be disposed to another location where they are autoclaved under low pressure steam for a predetermined time to sterilize them, then rebagged and taken to a landfill for burial.

Experience has taught that this disposal chain affords ample opportunity for unskilled personnel to be injured and/or contaminated by contact with used medical-surgical materials.

Thus, a problem created by the use-and-dispose philosophy is that of containing and disposing of the used materials, much of which includes dangerously sharp implements referred to as "sharps" in the field, both within the hospital environment and in the disposal chain.

Another and related problem is the safe containment until disposal of those sharps which might be put to illicit uses, e.g., hypodermic needles, were they to fall into unauthorized hands.

Exemplary thereof is the rigid disposable container of U.S. Pat. No. 4,842,138, issued Jun. 27, 1989 to Sandel, the disclosure of which is incorporated herein by this reference. In that invention, five plastic molded pieces were snapped together to form the disposable container.

It would be desirable to have an inexpensive, rigid, tamper resistant closure lid for attachment to a container for safely holding and disposing of the used medical-surgical material, which is itself entirely disposable, in keeping with the use-and-dispose philosophy.

SUMMARY OF THE INVENTION

It is therefore an object of the present invention to provide an inexpensive, simple, rigid but lightweight closure lid for attachment to a container for the storage and disposal of used medical-surgical materials.

It is yet another object of the present invention to provide such a closure lid for attachment to a container to hold and dispose of medical sharps safely and to prevent casual access to controlled implements, particularly hypodermic needles and syringes, by unauthorized persons.

It is still another object of the present invention to provide a closure lid for attachment to a container for used medical-surgical materials in a manner which prevents their contamination of the surrounding sterile area.

It is yet another object of the present invention to provide a closure lid for attachment to a container which may be disposed of simultaneously with the disposal of the used medical-surgical materials, thereby obviating the need to sterilize the container itself.

These objects and other advantages are preferably accomplished in a closure lid made of inexpensive, lightweight but rigid, disposable, injection molded plastic, comprising a top cover and slide closure which can be easily assembled together by unskilled personnel without the use of tools and attached to a rigid container to form the enclosure, the closure lid having a plurality of apertures through which used medical-surgical materials may be inserted one way into the container, including a larger aperture guarded by a one-way barrier which snaps shut after the insertion of larger used materials. The barrier is selectively removable by the user to provide a more "open" container, and flush mounting slide closure is provided, the position of which is adjustable by the user to close the openings of the container either partially during use or completely before disposal.

DESCRIPTION OF THE DRAWINGS

A more complete understanding of the invention may be obtained by a review of the following description of the preferred embodiment, when taken in conjunction with the drawings, wherein:

FIG. 3 is a sectional view of the closure lid with the slide closure shown in the fully open position, as revealed by section 3—3 taken in FIG. 1;

FIG. 4 is a view as in FIG. 3 with the slide closure shown in the fully closed position;

FIG. 5 is a partial section view through the side of the closure lid, as revealed by section 5—5 taken in FIG. 3;

FIG. 6 is a partial section view through the side of the closure lid, as revealed by the section 6—6 taken in FIG. 3;

FIG. 7 is a view of the top of the closure lid showing the slide closure in the fully open position;

FIG. 8 is a view of the underside of the top cover of the closure lid;

DESCRIPTION OF THE PREFERRED EMBODIMENT

Figure 1:
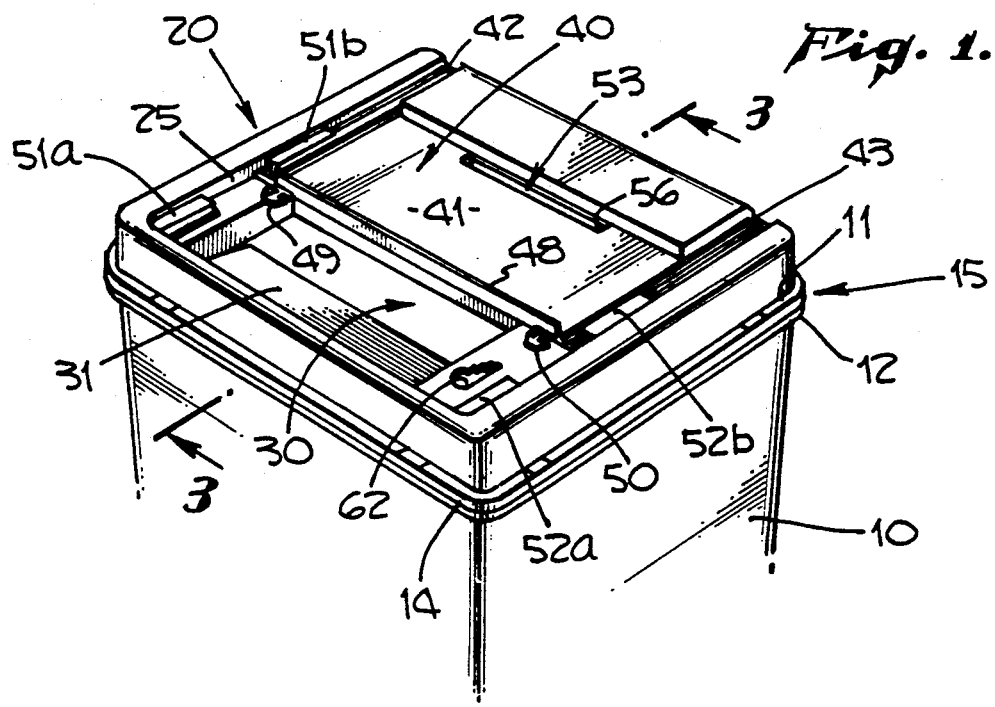
FIG. 1 is an isometric view of the closure lid assembled to a rigid container with the slide closure shown in the fully open position.

FIG. 1 best illustrates a preferred embodiment of the subject of the present invention, a closure lid 15 for attachment to a disposable container for medical sharps and other disposable medical-surgical waste materials, FIG. 1 being an isometric view of the closure lid 15 attached to container 10. Closure lid 15 comprises two snap-lock parts: a top cover 20 and slide closure 40.

It is contemplated that in the preferred embodiment of the closure lid 15, all parts are injection molded from a strong but lightweight, inexpensive thermoplastic such as polyethylene or polypropylene. This results in a closure lid that is relatively strong, rigid, decoratively colorful, but sufficiently inexpensive to warrant a one-use disposal.

Additionally, if top cover 20 and slide closure 40 are molded from a transparent or translucent material, the contents of the container may be easily viewed and the remaining available disposal volume easily estimated.

These modes and materials of fabrication also permit the inclusion of details within the molds to incorporate with the parts certain advantageous features discussed below, e.g., the "nesting" ability of the parts and the snap-lock fasteners of the closure lid 15. The thermoplastic material of the parts further permits the inclusion of a very smooth, finished surface on both the inside and the outside of the container, which helps to prevent the entrapment of potentially septic material on the internal or external surface of the closure lid 15.

Container 10, as commonly known in the art, consists essentially of an enclosure with an open top having a seating flange 12 at the periphery thereof for mating with a similar top flange 11 on top cover 20. A peripheral wall 14 encircles the periphery of seating flange 12 and aids in lending strength and rigidity to the seating flange 12, while serving as a guide for assembly with top cover 20.

Figure 10:
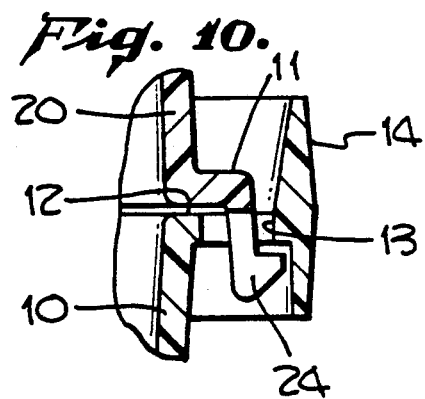
FIG. 10 is a detailed sectional view through the top to bottom fastener mechanism.

Disposed about top flange 11 are a plurality of snap-lock fastening means. The detail of these fasteners is best illustrated in FIGS. 3 and 10, and include a female opening 13 in seating flange 12 to receive mating, over-center male members 24 located on the top cover 20. However, when the parts are once snapped together, they are not easily disassembled without some effort and the use of tools, which renders the contents of the container relatively tamper-resistant.

Top cover 20 consists of an enclosure with an open bottom having a top flange 11 encircling its entire periphery. Molded into the upper surface of top cover 20 are a pair of recesses, 25 and 37. The lower recess 37 includes a large opening 30 through which larger medical-surgical materials may be inserted into container 10, as well as a smaller opening 62 having specialized, tool-gripping surfaces molded in its periphery to permit its engagement of, and the disengagement of, certain medical sharps from their associated devices. In the embodiment illustrated, opening 62 comprises an aperture for Luer-type hypodermic needles of various sizes. By inserting a hypodermic needle mounted onto a hypodermic syringe into opening 62, by simply twisting the syringe in an anti-clockwise direction, the user may cause the needle to be disengaged from the syringe, whereby it will fall into the disposal volume of container 10. This enables the disposal of the used hypodermic needle while permitting the syringe to be retained for sterilization and further use by those institutions which have not switched to completely disposable hypodermic syringes. The entire used syringe and needle may be disposed of through larger opening 30.

The large opening 30 on top cover 20 is provided with a rectangular barrier flap 31, molded into top cover 20 at the level of the large opening 30, which is attached at one edge to permit the flap to swing inwardly into the container when used medical-surgical materials are inserted therethrough. Barrier flap 31 covers a portion of large opening 30 and guards the internal volume of container 10 against the egress of discarded materials and renders the large opening 30 of container 10 relatively tamper-resistant. However, if desired, barrier flap 31 may be removed by the user to provide an unimpeded large opening 30 into container 10, a feature which may be desirable from the standpoint of some practitioners. To accomplish this, barrier flap 31 is provided with a series of serrations at the hinged edge where it joins with top cover 20. By repeated flexing of barrier flap 31 back and forth within large opening 30, the flap can be broken off to provide an unimpeded opening 30.

The upper recess 25 of top cover 20 provides a manipulating surface for a flush slide closure 40. Slide closure 40 is provided with a right angled, vertical upstanding flange 48 at the front edge of the slide closure, which functions as a handle and stops against the front sidewall 32 of upper recess 25 in the cover closed position.

Slide closure 40 is additionally provided with a rear end interlocking means, indicated generally at 53, which forms a rigid seal between the back edge 45 of the slide closure 40 and lower recess 37 of top cover 20. The exemplary rear end interlocking means comprises a slide flange 55, a lock tab aperture 56, and a depending rear wall 54 integrally molded on the slide closure 40, and a locking flange 39 and upstanding rear wall 35 integrally molded on the top cover 20. With the slide closure 40 in the fully closed position, locking flange 39 enters into lock tab aperture 56 above slide flange 55, and upstanding rear wall 35 comes into contact with depending rear wall 54. In this configuration, any downward pressure applied to the lower recess 37 brings the locking flange 39 into contact with the slide flange 55, which prevents the opening of any gaps between upstanding rear wall 35 and depending rear wall 54. Therefore, a rigid seal is maintained between the back edge 45 of slide closure 40 and top cover 20 when the slide closure 40 is in the fully closed position, and the inadvertent expulsion of disposed medical-surgical material from between slide closure 40 and top cover 20 is precluded.

Figure 2:
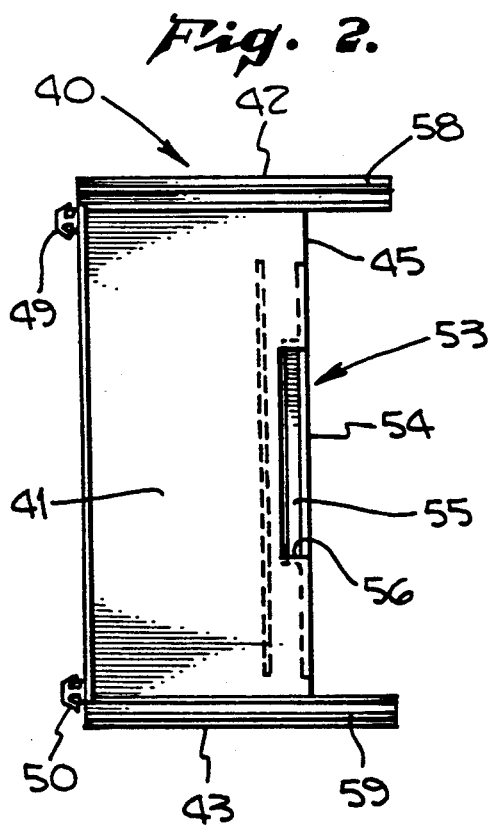
FIG. 2 is a view of the top of the slide closure.

Integrally molded on slide closure 40 is a pair of runners 42 and 43, best illustrated in FIG. 2. Each runner has an upstanding runner flange 58 and 59 extending the length of the runners. Integrally molded on the top surface 21 of top cover 20 are a plurality of runner retention flanges 51a, 51b and 52a, 52b, best illustrated in FIGS. 1 and 7. Each of the runner retention flanges, such as 51a, has a depending flange 63a, b, c and d, which serve to overlap and retain the runners 42 and 43, enabling the slide closure 40 to be manipulated to vary the size of opening 30, illustrated in FIGS. 1, 6 and 7.

Figure 9:
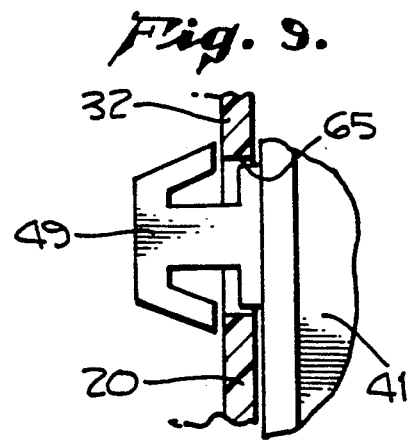
FIG. 9 is a detailed section through the closure lid revealed by the section 9—9 taken in FIG. 4, showing the two-prong locking spear tabs in the permanently locked position.

In the fully closed position, as shown in FIGS. 4 and 9, slide closure 40 is "locked" in position by a pair of two-prong locking spear tabs 49 and 50 which firmly engage a pair of front wall apertures 65 and 66, shown in FIG. 8. It is intended by this arrangement to prevent the slide closure 40 from being easily reopened, rendering the container 10 more tamper-resistant and leak-proof after the container has been filled and is ready for disposal.

Top cover 20 is provided with a pair of vent opening 60 and 61, best shown in FIG. 8, such that when side closure 40 is in the fully closed, locked position the vent openings are exposed. The contents of container 10 may then be autoclaved with steam for sterilization of the contents prior to disposal, as required by law in some states.

Another product of the molding process and plastic materials selected for closure lid 15 is the presence of draft angles incorporated into the parts as a consequence of the necessity for the removal of the parts from the mold. This draft angle may be utilized advantageously to permit the top cover part 20 to be "nested" or stacked within one another for handling and shipment, for convenience, and to conserve shipping volume.

Those skilled in the art will recognize that the foregoing materials, methods of fabrication and detail features are suggested for illustration purposes only, and can be suitably modified to provide a variety of disposable container shapes, styles and functions.

Accordingly, our invention, a closure lid for attachment to a container for holding and disposing of used medical-surgical materials and sharps, should be limited in its scope only by the appended claims.

We claim:

1. A closure lid which attaches to a rigid container for holding and disposing of used surgical sharps and other disposable medical-surgical waste materials, comprising:

a molded plastic top cover for rigidly enclosing a space within said container to contain said disposed medical-surgical waste materials, said top cover having at least one aperture to permit the insertion of said medical-surgical waste materials therethrough into said space, a first recess having a plurality of integrally molded runner retention flanges and a second recess having a centrally located locking flange;

a molded plastic slide closure movably attached to said top cover for varying the size of said at least one aperture from a fully open to a closed position and for permanently sealing said container, said slide closure having a plurality of runners captured by said runner retention flanges to guide manipulation of said slide closure and a rear end interlocking means for engaging said locking flange to form a rigid seal with said top cover upon manipulation of said slide closure to the fully closed position.

2. The closure lid of claim 1 further comprising at least one additional aperture through said top cover having a sharps engaging surface molded into its periphery to grasp said sharps for disengagement of said sharps from an associated medical-surgical device, whereby the sharps may fall through said at least one additional aperture into said container.

3. The closure lid of claim 1 further comprising a one-way barrier in said at least one aperture and comprising a single closure flap molded into said top cover along one edge of said flap to hinge said flap for inward deflection with respect to said top cover upon insertion of said medical-surgical materials therethrough, said closure flap extending substantially entirely across said aperture in a direction parallel to said one edge and only partially across said aperture in a direction perpendicular to said one edge.

4. The closure lid of claim 1 wherein said top cover and said slide closure are fabricated from a transparent or translucent material such that the contents of said container may be visualized.

5. The closure lid of claim 1 wherein said slide closure is provided with a plurality of two-prong locking spear tabs, and said top cover is provided with a plurality of front wall apertures positioned relative to said spear tabs, whereby said spear tabs engage said front wall apertures upon manipulation of said slide closure to the fully closed position permanently locking said slide closure in the fully closed position.

6. The closure lid of claim 1 wherein said top cover is provided with a plurality of steam vents positioned on the central surface of said top cover, whereby said steam vents are fully exposed upon manipulation of said slide closure to the fully closed position.

7. The closure lid of claim 1 wherein:

said rear end interlocking means of said slide closure comprises a slide flange, a lock tab aperture above said slide flange, and a depending wall integrally molded onto said slide closure; and said locking flange is integrally molded with a rear wall of said top cover; whereby upon manipulation of said slide closure to the fully closed position, said locking flange enters into said lock tab aperture above said slide flange, and said rear wall engages said depending wall forming a rigid seal between said slide closure and said top cover, such that inadvertent expulsion of disposed medical-surgical material from between said slide closure and said top cover is precluded.

8. A closure lid which attaches to a rigid container for holding an disposing of used surgical sharps and other disposable medical-surgical waste materials, comprising:

a molded plastic top cover for rigidly enclosing a space within said container to contain said disposed medical-surgical waste materials therethrough into said space, said top cover having a least one aperture to permit the insertion of said medical-surgical waste materials therethrough into said space, a first recess, a second recess having a centrally located locking flange, a central surface and a plurality of steam vents positioned on the central surface of said top cover; and a molded plastic slide closure movably attached to said top cover for varying the size of said at least one aperture from a fully open to a closed position and for sealing said container, said slide closure having a rear end interlocking means for engaging said locking flange to form a rigid seal with said top cover upon manipulation of said slide closure to the fully closed position, said steam vents being fully exposed upon manipulation of said slide closure to the fully closed position.

* * * * *